United States Patent
Wissmann

(10) Patent No.: US 11,504,204 B2
(45) Date of Patent: Nov. 22, 2022

(54) STERILE CONTAINER HAVING A CLOSURE SYSTEM

(71) Applicant: AESCULAP AG, Tuttlingen (DE)

(72) Inventor: Helmar Wissmann, Owingen (DE)

(73) Assignee: AESCULAP AG, Tuttlingen (DE)

( * ) Notice: Subject to any disclaimer, the term of this patent is extended or adjusted under 35 U.S.C. 154(b) by 428 days.

(21) Appl. No.: 16/495,016

(22) PCT Filed: Apr. 16, 2018

(86) PCT No.: PCT/EP2018/059667
§ 371 (c)(1),
(2) Date: Sep. 17, 2019

(87) PCT Pub. No.: WO2018/192875
PCT Pub. Date: Oct. 25, 2018

(65) Prior Publication Data
US 2020/0281679 A1 Sep. 10, 2020

(30) Foreign Application Priority Data

Apr. 20, 2017 (DE) .......................... 102017108411.8

(51) Int. Cl.
*A61B 50/00* (2016.01)
*A61L 2/26* (2006.01)
*B65D 45/24* (2006.01)

(52) U.S. Cl.
CPC ................ *A61B 50/00* (2016.02); *A61L 2/26* (2013.01); *B65D 45/24* (2013.01);
(Continued)

(58) Field of Classification Search
CPC ... A61B 50/00; A61B 2050/0074; A61L 2/26; A61L 2202/121; A61L 2202/182; B65D 45/24
(Continued)

(56) References Cited

U.S. PATENT DOCUMENTS 4,748,003 A * 5/1988 Riley .................. A61L 2/26
137/493.7
4,818,502 A 4/1989 Taschner
(Continued)

FOREIGN PATENT DOCUMENTS

DE 9203630 U1 6/1992
DE 202015103523 U1 8/2015
(Continued)

OTHER PUBLICATIONS

German Search Report for German Application No. 10 2017 108 411.8, with English translation, dated Jan. 5, 2018—14 pages.

*Primary Examiner* — J. Gregory Pickett
*Assistant Examiner* — Niki M Eloshway
(74) *Attorney, Agent, or Firm* — Christopher A. Rothe; Culhane Meadows, PLLC

(57) ABSTRACT

A medical or surgical sterile container includes a first container part, a second container part, and at least one closure system arranged on the second container part which is pivotable between a closed position, in which the first container part and the second container part are locked to each other by the closure system, and an open position, in which the first container part and the second container part are unlocked. The first container part has an integrally formed edge portion on which the closure system is immediately supported in the closed position, for transferring a closing force of the first container part to the second container part.

20 Claims, 4 Drawing Sheets

Figure 1:
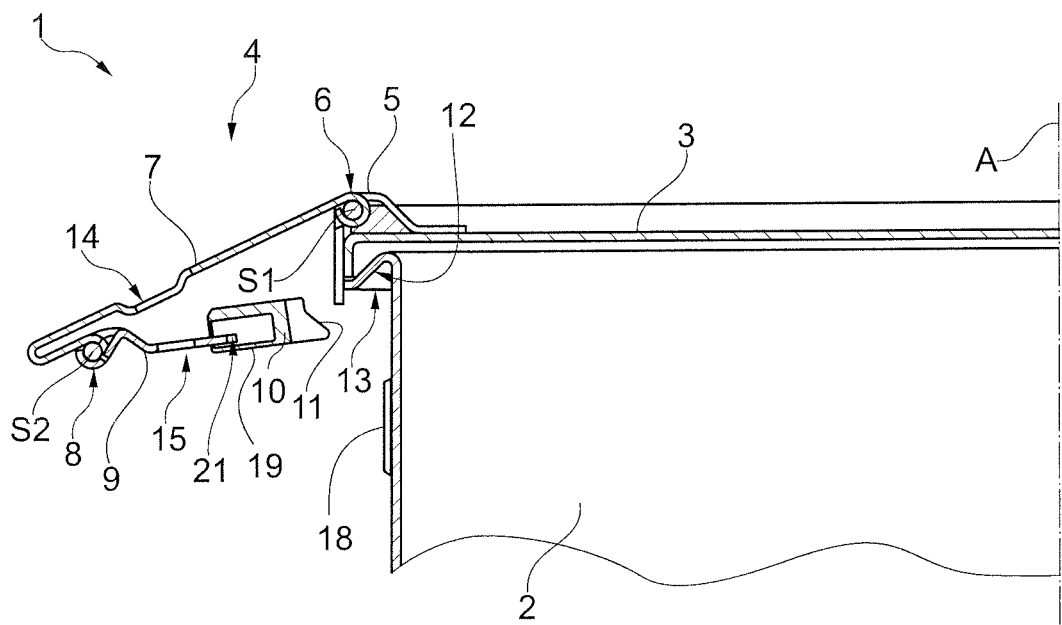

(52) U.S. Cl.
CPC . *A61B 2050/0074* (2016.02); *A61L 2202/121* (2013.01); *A61L 2202/182* (2013.01)

(58) Field of Classification Search
USPC ......................................................... 220/326
See application file for complete search history.

(56) References Cited

U.S. PATENT DOCUMENTS

| | | | | |
|---|---|---|---|---|
| 6,371,326 | B1* | 4/2002 | Gabele | A61L 2/26 206/373 |
| 8,590,724 | B2* | 11/2013 | Kreidler | A61B 50/30 220/324 |
| 10,434,206 | B2* | 10/2019 | Thomas | A61L 2/26 |
| 2006/0286005 | A1 | 12/2006 | Bauer | |
| 2013/0043250 | A1* | 2/2013 | Kreidler | A61L 2/26 220/324 |
| 2013/0175276 | A1 | 7/2013 | Gleichauf et al. | |
| 2015/0004075 | A1 | 1/2015 | Gray-Dreizler et al. | |
| 2016/0213115 | A1 | 7/2016 | Gonitianer et al. | |
| 2016/0302544 | A1* | 10/2016 | Tonelli | B65D 45/24 |
| 2017/0360976 | A1 | 12/2017 | Thomas et al. | |
| 2019/0177059 | A1* | 6/2019 | Yang | B65D 25/32 |
| 2021/0282879 | A1* | 9/2021 | Thomas | A61B 50/30 |

FOREIGN PATENT DOCUMENTS

| | | |
|---|---|---|
| WO | 2010023702 A1 | 3/2010 |
| WO | 2012038314 A1 | 3/2012 |
| WO | 2013131761 A2 | 9/2013 |
| WO | 2015039868 A1 | 3/2015 |
| WO | 2016083595 A1 | 6/2016 |

* cited by examiner

STERILE CONTAINER HAVING A CLOSURE SYSTEM

CROSS REFERENCE TO RELATED APPLICATIONS

This application is the United States national phase entry of International Application No. PCT/EP2018/059667, filed Apr. 16, 2018, which claims the benefit of priority of German Application No. 10 2017 108 411.8, filed Apr. 20, 2017. The contents of International Application No. PCT/EP2018/059667 and German Application No. 10 2017 108 411.8 are incorporated by reference herein in their entireties.

FIELD

The invention relates to a medical or surgical sterile container having a first sterile container part, in particular a trough-like container vessel as well as having a second sterile container part, in particular a container lid/container cover, and having at least one closure system/closure arranged on the second container part, in particular in the manner of a toggle lever or a spring-preloaded closure system, which is pivotable/switchable between a closed position, in which the first container part and the second container part are locked together by means of the closure system, and an open position, in which the first container part and the second container part are unlocked.

BACKGROUND

Containers with a closable container lid, which are closed and locked via at least one closure, are used, inter alia, for the storage and transport of objects which are to be securely separated from the environment. In particular medical/surgical sterile containers with at least one closure are used in medicine, in particular in surgery, for example to sterilize surgical instruments, implants and the like and to store and transport them temporarily after sterilization. The objects to be sterilized are arranged in the interior of the container vessel and locked and closed with the container lid via the closure or the closures. The container, including the objects to be sterilized accommodated in it, is then usually transferred to a sterilizer, in which the interior of the container vessel is treated with a sterilizing gas. In order to prevent recontamination after sterilization and to ensure sterility of the objects stored in the container, the containers are usually sealed with a seal after sterilization.

From WO 2016/083595 A1, a closure system or closure for a medical sterile container is known having a trough-like first container part (container vessel) and a lid-like second container part (container lid). The closure is arranged at one of the container parts and can be pivoted between a closed position, in which the two container parts are locked together, and an open position, in which the two container parts are unlocked. The closure has a translationally shiftable locking member on a closure flap of the closure system, which in the closed position engages in a counter element attached to the other container part and securely locks and closes the two container parts together.

Also known from the utility model G 92 03 630.9 is a tension lock for surgical sterilization containers with a trough-shaped first container part and a lid-shaped second container part, whereby in a closed position the tension closure engages behind and locks a locking hook provided on a container part. This locking hook is preferably attached to the container part as a bent base plate.

With known (sterilization) containers and closure systems, the disadvantage is that in addition to the two essential container parts, a separate counter element is required for locking in order to receive a closing force/locking force. Due to the additional counter element, further production and assembly steps are necessary, and if the counter element is connected to a container part, due to the connection, the container is more susceptible to leakage and associated sterilization problems, to mechanical stress peaks, and to a loss of the connection of the counter element to the container itself, e.g. in the case of an adhesive connection.

SUMMARY

Based on the prior art described above, the invention is based on the object to remove or at least reduce the disadvantages of the prior art, and in particular to provide a medical or surgical sterile container, and a closure system which is simple and secure to close and lock, which has a reliable protection against unintentional opening, which has a simple construction of the closure system, and which does not require a separate counter element on one of its container parts in order to receive a closing force and to lock the two container parts together in a closed position.

This object is solved according to the invention in that the first container part has a (material-) integrally formed (crimped/folded) edge portion (which thereby forms an undercut), on which the closure system is immediately/directly (loosely/freely) supported in the closed position for transferring a closing force/locking force of the first container part to the second container part. Using the edge portion, the medical or surgical sterile container can be locked in this way without requiring a separate counter element which has to be attached or tied to the first container part. This reduces the risk of leakage, increases the service life of the medical or surgical sterile container, and improves the secure locking of the medical or surgical sterile container.

In an advantageous embodiment, the first container part can have a container-contour portion which is in particular formed as a completely circumferential edge/collar and which preferably has/forms an undercut, and the closure system can have a closure-contour portion which is shaped/formed at least in sections to be complementary to the container-contour portion in order to flatly abut on the container-contour portion/undercut and to engage in a form-fitting manner in order to securely lock the first container part and the second container part together in the closed position. The container-contour portion can be easily and directly integrated into the edge portion of the container during production, for example in the form of a folded flange during deep drawing. The closure-contour portion can be shaped complementarily to the container-contour portion in sections, so that when the container is locked, the closure-contour portion engages in the container-contour portion in a form-fitting manner and transfers a closing force.

In a further embodiment, the edge portion of the first container part may be made of a metallic material/substance or a metal or alloy, which in particular is deep-drawn or can be deep-drawn.

It is particularly advantageous if the closure system is prepared to accommodate a seal/security seal which secures the closure system against accidental opening/unlocking when sealing in the closed position. In particular, it may be possible that a seal cannot be accommodated or arranged in the closure system if the closure system is not correctly locked, i.e. it is only possible to seal the medical or surgical sterile container if it is correctly locked. The seal is inevitably destroyed when the locking system is opened, so that a medical or surgical sterile container with an undamaged seal has certainly not been opened.

In an embodiment, the closure system may be attached to/arranged at the second container part by means of a closure base, and the closure base may have formed therein a first pivot joint/pivot element with a first pivot axis/hinge axis, to which a closure flap is pivotably attached, and the closure flap may comprise a second pivot joint with a second pivot axis, which is essentially parallel to the first pivot axis, to which a closure lever is pivotably connected, and the closure lever is at an end region supported, in particular in a form-fitting manner, on the edge portion of the first container part, in order to receive a closing force of the closure system in the closed position and to securely lock the first container part and the second container part together. This configuration with the above components and their arrangement form the toggle-lever joint in order to press the two container parts against each other via a power transmission by means of a lever arm, in this case indirectly via the closure flap, and then to lock them securely in the closed position.

In other words, the closure element has two arms coupled to each other in a joint/hinge manner, preferably in plate form, of which one arm is jointed/hinged to the second container part (preferably in its edge region) and the second (freely pivotable) arm has at its free end a support foot which engages in the undercut on the first container part. If the first arm is folded down on the second container part while the support foot is already supported on the undercut, it is pressed against the undercut in the manner of a toggle-lever mechanism and thus pulls the second container part against the first container part. The closure system can be designed in such a way that one arm can be pivoted beyond the bottom dead center against the wall of the first container part, thus enabling the closure system to lock itself.

It is advantageous if the first pivot joint and/or the second pivot joint of the closure system is formed by an elastic portion. An elastic portion with a defined pivot axis, e.g. using fiber-composite laminate composites with corresponding fiber orientations, allows an integral formation so that, for example, production and assembly can be simplified and, in particular, less deposit space is available for germs and bacteria.

It is furthermore particularly advantageous if the first pivot joint and/or the second pivot joint of the closure system is formed by a hinge, preferably with at least one joint plate and a corresponding pivot pin. Hinges are well known, inexpensive, and simple to assemble.

It has proven to be useful if the closure system with the closure flap, the closure lever, and the seal is designed in such a way that the seal fixes the closure flap with the closure lever rigidly together when sealing in the closed position in order to secure the closure system against accidental opening in this way. The seal only engages the closure flap and the closure lever without, for example, requiring a connection to the container parts.

It is advantageous if a pivoting movement of the closure flap relative to the closure base and/or a pivoting movement of the closure lever relative to the closure flap can be limited to allow simple and efficient locking. This can be done, for example, by a stop formed on the closure base and/or on the closure flap and/or on the closure lever. In order to avoid that the closure lever first has to be brought into the correct position by hand/manually in order to pivot the closure system into the closed position, the range of a pivot movement of the closure lever in relation to the closure flap is defined. Thus, the closure system can be pivoted directly into and out of the edge portion of the container or the closure flap can be used as handles in the open position.

In a further advantageous embodiment, a spring element, e.g. in the form of an elastic material or a spring, can be provided or connected between the closure lever and the closure contour portion, wherein this spring element in the closed position of the closure system pre-stresses one container part against the other container part in order to secure the closure system against unintentional opening, to implement/integrate an integrated valve function against an inadmissible internal pressure of the container, and to ensure tolerance compensation. Due to the mechanics/mechanical embodiment of the closure system, the closing force initially increases when the closure system pivots from the closed position to the open position in order to prevent unintentional opening. At the same time, an admissible internal pressure of the container can be defined via the spring element, since the spring force also defines the closing force and counteracts the internal pressure of the container. If the internal pressure is exceeded, the two container parts are no longer kept closely on top of each other by the spring force of the spring element, so that a fluid can escape and the excess pressure drops to the admissible internal pressure. The spring element can also be used to ensure tolerance compensation, since tolerances can occur during the production of the container or when the container parts are changed.

In even other words, the invention relates to a medical or surgical sterile container with two container parts with an, in particular spring-loaded, closure without an additional counter element by using the medical or surgical sterile container geometry or the geometry/contour of a first container part (container-contour portion). The medical or surgical sterile container according to the invention with the closure system uses the medical or surgical sterile container geometry or a selected contour on the medical or surgical sterile container (edge portion with container-contour portion/collar on the first container part) to receive a closing force. A spring element sits directly on the closure lever instead of, as known, on the closure flap. The, in particular spring-loaded, closure system is secured against unintentional opening.

The closure system comprises in particular a closure flap, a closure lever, a spring-loaded contour part, two pivot axes, two pivot joints, with joint plates and a fastening element (pivot pin), and a seal.

At this point, the distinction between the terms shut state and locked/closed state shall be addressed as well. The shut state of the container merely describes that the two container parts rest on each other and thus that the container opening is shut, whereby one container part can be moved relative to the other container part at any time and the medical or surgical sterile container can be opened. The closure system is in the open position.

The locked/closed state is understood to be the state of the container in which the closure system in the closed position securely locks the two container parts together.

BRIEF DESCRIPTION OF THE DRAWING FIGURES

Figure 2:
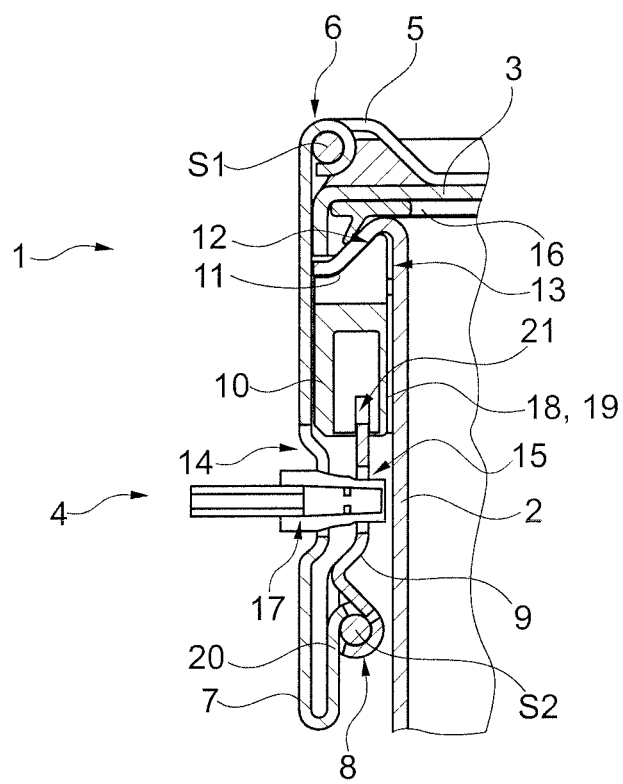
Figure 3:
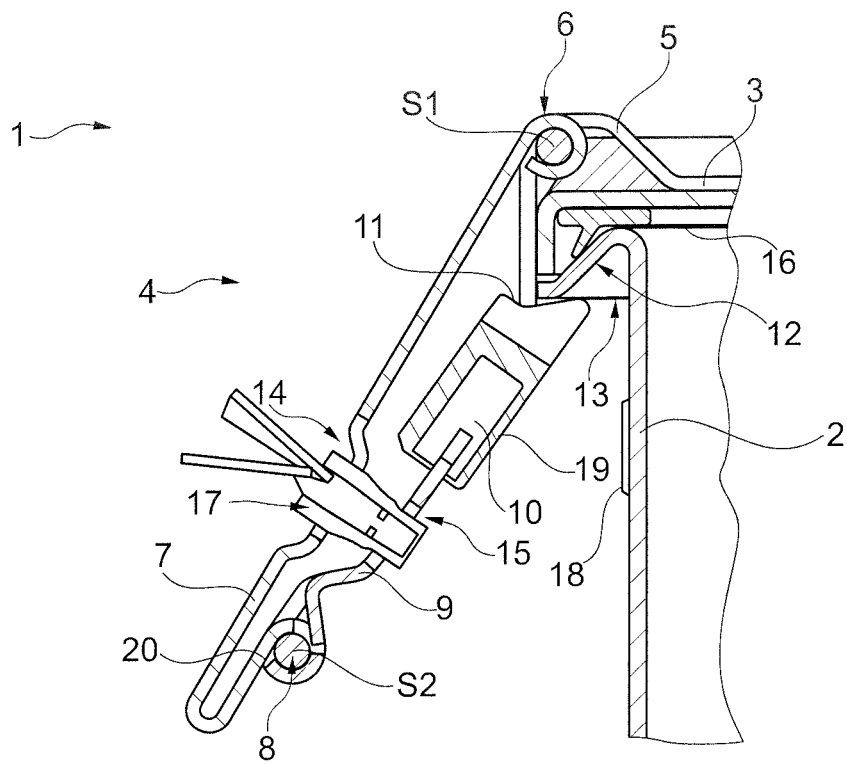
Figure 4:
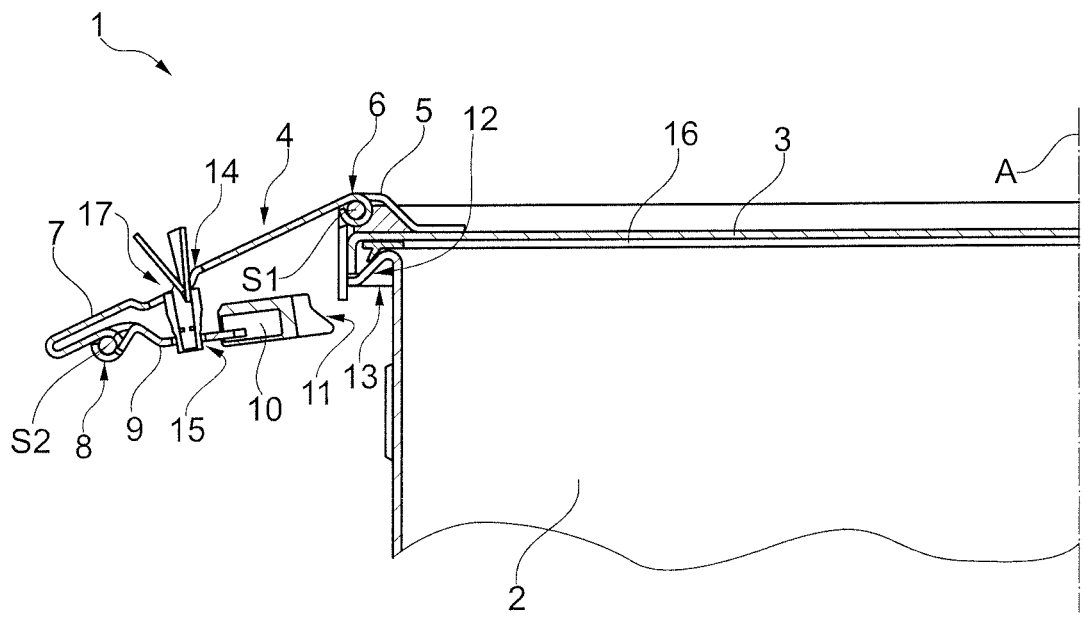
Figure 5:
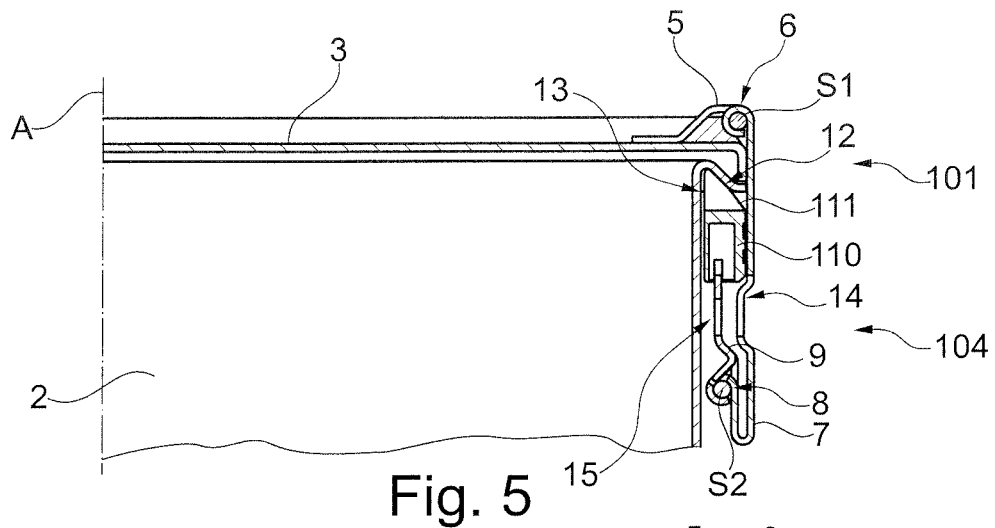
Figure 6:
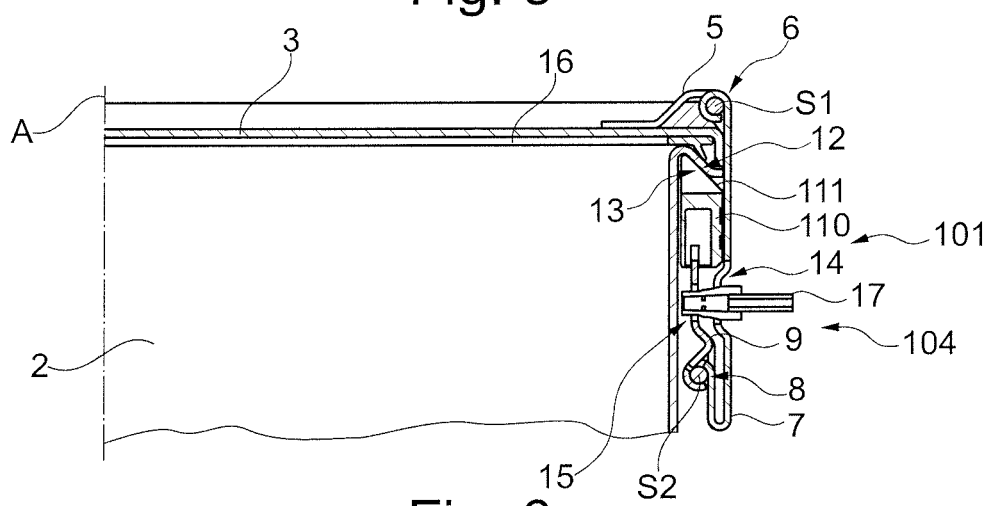
Figure 7:
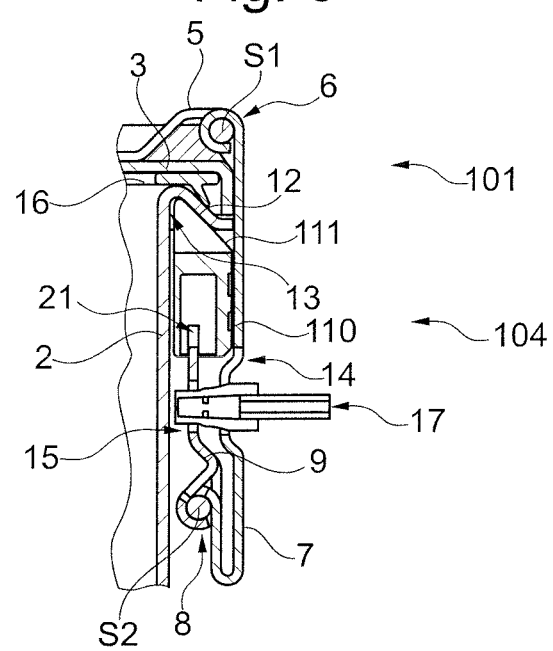
Figure 8:
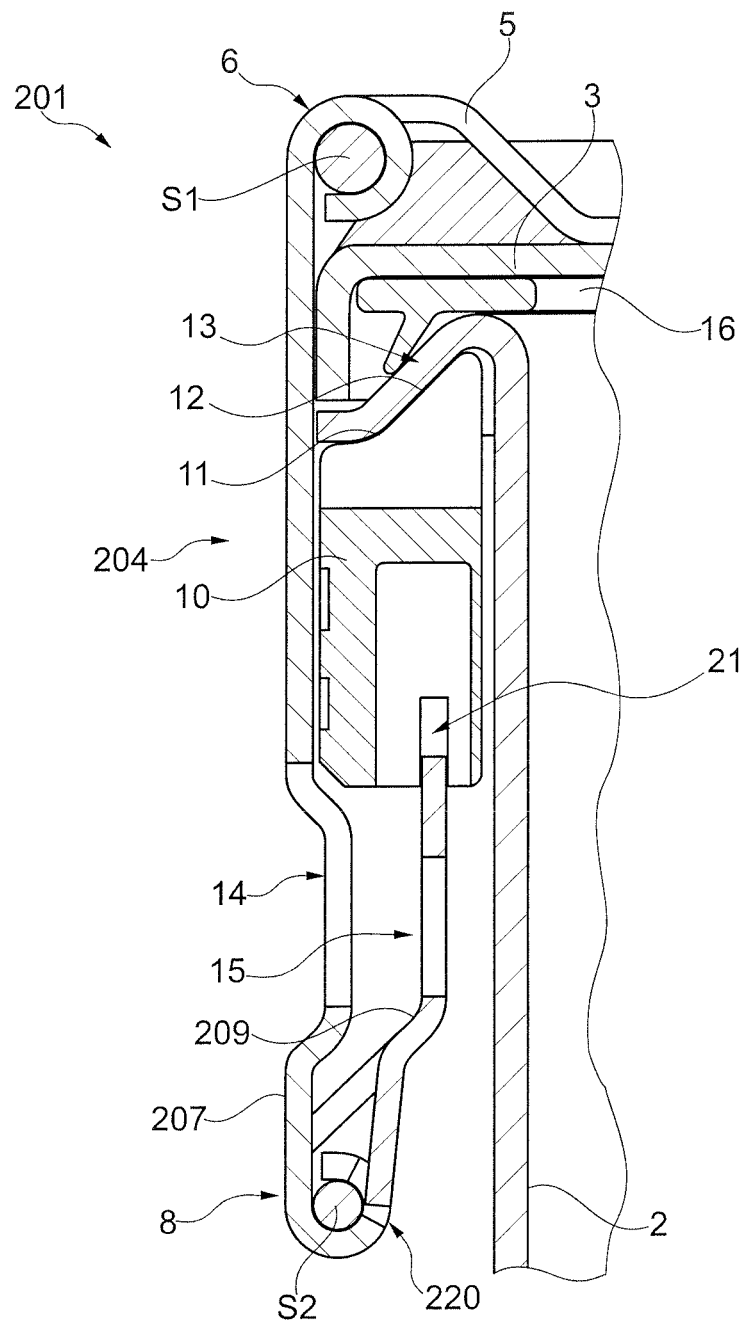

The invention is explained in more detail below using preferred embodiments with the help of figures. These show:

FIG. 1 shows in a cross-section a side view of a relevant section (partial section view) of a medical or surgical sterile container according to the invention according to a first preferred embodiment, wherein the medical or surgical sterile container is in a shut but still unlocked state or an open position, FIG. 2 shows a partial section view of the medical or surgical sterile container from FIG. 1 with inserted seal ring and inserted seal, whereby the closure system is in a closed position and the two container parts are securely locked together, FIG. 3 shows a partial section view of the medical or surgical sterile container from FIG. 2, whereby the closure system was unlocked and pivoted further in the direction of the open position and a closure-contour part was pivoted out of an edge portion of the first container part, FIG. 4 shows a partial section view of the medical or surgical sterile container from FIG. 2 and FIG. 3, with the closure system being in the open position, FIG. 5 shows a partial section view of a medical or surgical sterile container according to a second preferred embodiment in the closed position, in which a closure-contour portion of the closure-contour part has a further configuration, FIG. 6 shows a partial section view of the medical or surgical sterile container from FIG. 5 with inserted seal ring and inserted seal, FIG. 7 shows a partial section view of the closure system from FIG. 6, and FIG. 8 shows a partial section view of a medical or surgical sterile container according to a third preferred embodiment, in which the closure system has a further configuration, in a closed position.

The figures are schematic in nature and only serve to understand the invention. The same elements are provided with the same reference signs. The features of the different embodiments can be exchanged with each other.

DETAILED DESCRIPTION

FIGS. 1-4 show a sterile container 1 according to the invention of a first preferred embodiment in a partial section view, which is designed as a medical or surgical sterile container.

FIG. 1 shows the sterile container 1 in an unlocked state or in an open position. The sterile container 1 has a trough-like and cylindrical first container part 2 in the form of a container vessel with a container wall/walling and a container bottom which is not shown, similar to a (cooking) pot, which is rotationally symmetrical about an axis A or rectangular. On a circular or rectangular opening of the container vessel 2, lies an essentially disc-shaped/plate-shaped and lid-like second container part 3 in the form of a container lid corresponding to the container vessel 2. The container lid 3 completely closes the opening of the container vessel 2 in that a circumferential frame is formed on the lid 3 which encloses the container vessel 2 on the outside.

In order to securely close or lock the container vessel 2 with the container lid 3, the sterile container 1 has a closure system 4 in the manner of a toggle-lever construction. Opposite to the closure system 4 shown in FIG. 1 or symmetrically to axis A, a second closure system 4 is arranged which is not shown. The closure system 4 engages both container parts 2, 3 and presses them against each other in the locking or closed position.

The closure system 4 is connected, in particular by means of rivets, to the container lid 3 by means of a closure base (link base) 5, which is designed as a bent metal sheet/shaped sheet-metal part, at an area running perpendicular to axis A or parallel to the closing surface of the container lid 3. The closure base 5 can also be welded instead of using rivets. The closure base 5 protrudes above the container lid 3 in the direction of the top as well as in the direction of the lid rim, and a bent portion lies with a surface parallel to the axis A at the rim of the container lid 3 (at the outside). A closure flap 7 is connected at the closure base 5 via a first pivot joint 6 in the form of a hinge by means of joint plates formed on the closure base 5 and a pivot pin to be pivotable about a first pivot axis S1. The first pivot axis S1 lies (essentially) parallel to the closing surface of the container lid 3 or is perpendicular and offset to axis A.

The closure flap 7 is designed as a bent metal sheet and has a 180° bending (U-shaped bending) at the end portion facing away from the first pivot joint 6, so that a free end portion of the closure flap 7 lies closer to the walling of the container vessel 2 in a closed position (see FIG. 2) and is covered radially on the outside by a portion of the closure flap 7. Thus, a simple handle is formed. The first pivot joint 6 is arranged on the closure base 5 at an outside (lid rim) and above the container lid 3 or the side of the container lid 3 facing away from the container vessel 2. Furthermore, the first pivot joint 6 essentially lies, seen parallel to axis A, in the extension of the circumferential outer side of the container lid 3. This arrangement of the first pivot joint 6 allows in the closed position a direct force transmission of the closing force of the two container parts 2, 3 essentially parallel to the axis A and essentially perpendicular to the plane of the opening of the container vessel 2. In particular, the closing force does not run exactly parallel to the axis A, but slightly obliquely from radially further inwards on the container vessel 2, which is arranged further down relative to the container lid 3, towards radially further outwards on the container lid 3. This results in self-locking or pre-stressing of the closure system 4 in the closed position (see FIG. 2).

The closure flap 7 has a second pivot joint 8 at its free end with a second pivot axis S2 lying parallel to the first pivot axis S1. At the second pivot joint 8, a closure lever 9 formed as a bent metal sheet is pivotably attached. The toggle-lever function of the executed closure system 4 is implemented via the closure base 5, the closure flap 7 pivotably connected via the first pivot joint 6, and the closure lever 9 pivotably connected via the second pivot joint 8.

At the free end of the closure lever 9, a closure-contour part (support foot) 10 is spring-mounted via a spring element 21 in the form of an elastic material in the longitudinal axis direction of the closure lever 9. The closure-contour part 10 has a guide in which the closure lever 9 is translationally guided. On the closure-contour part 10, a closure-contour portion 11 is formed on the side facing away from the closure lever 9. This closure-contour portion 11 corresponds in its contour/geometric form to a complementary container-contour portion (collar) 12 of an edge portion 13 of the container vessel 2 in order to securely lock the sterile container 1 as explained below. The spring element 21 in this embodiment is made of an elastic, rubber-like material and can alternatively also be a compression spring, or a spiral spring or the like. The closure part 10 including the closure-contour portion 11 can be manufactured as an injection-molded plastic component.

The closure flap 7 has a first recess (through-hole) 14, viewed along its longitudinal axis in a centrally-located portion, with an indentation formed or bent towards axis A as seen in the closed position (see FIG. 2), wherein the longitudinal axis of this first recess 14 points towards axis A in the closed position. The closure lever 9 also has a second recess (through-hole) 15 whose longitudinal axis in the closed position also points towards axis A and in the closed position is essentially congruent with the first recess (see FIG. 2). The recesses 14, 15 are used to accommodate a seal 17, as described below.

The container vessel 2 has a defined container contact surface 18 on the outside of the walling, which is formed as a flat surface and is parallel to the axis A. On the closure-contour part 10, a closure-contour part contact surface 19 is also formed as a flat surface on the side facing the container vessel 2. In the closed position of the closure system 4 (see FIG. 2), the container contact surface 18 and the closure-contour part contact surface 19 lie flat on each other and define an end position of the closed position. The container contact surface 18 in this embodiment is integrally formed as a beading in the wall of the container vessel 2. Alternatively, the container contact surface 18 can also be a separately attached component. In particular, the plane walling of the container vessel 2 itself, without any further formations, represents the container contact surface 18.

FIG. 2 shows the sterile container 1 from FIG. 1 in a closed position, wherein here, between the container vessel 2 and the container lid 3, a circumferential, disc-shaped seal ring 16 is inserted as a seal with an outer sealing lip with regard to the axis A (see FIG. 1) on the edge portion 13, in order to close the two container parts 2, 3 of the sterile container 1 together in a gas-tight manner. The interior of the sterile container 1 is hermetically sealed against its surroundings, with the exception of any filters and filter openings which may be present but which are not shown in the figures. In the closure system 4, a sealed seal 17 is inserted through the first and second recesses 14, 15.

The closed position of the closure system 4 was achieved by, starting from the state shown in FIG. 1, pivoting the closure flap 7 further around the first pivot axis S1 towards the closed position, for example by applying force with the thumb towards the axis A on the end of the closure flap 7 remote from the first pivot axis S1 by pressing. The closure-contour portion 11, which has an outer portion perpendicular to the axis A with a convexly curved transition to an inner portion of essentially 45 degrees to the axis A, has consequently slid into the container-contour portion 12 and pivoted into it and now lies flatly and in a form-fitting manner on or against it. The two contact surfaces 18, 19 lie flatly against each other. The closure flap 7 as well as the closure lever 9 or their longitudinal axes are essentially parallel to each other and parallel to the axis A. The closing force of the closure system is ideally transmitted, since the force essentially runs perpendicular to the plane of the opening of the container vessel 2 or parallel to the axis A in order to press the two container parts 2, 3 against each other.

In order to securely fix the closure system 4 in the closed position, the closure system 4 is sealed by the seal 17. The seal 17 engages the closure flap 7 on the one hand and the closure lever 9 on the other. After sealing, it fixes the closure flap 7 and the closure lever 9 rigidly together, so that an opening movement of the closure system 4 with an accompanying pivoting movement of the second pivot joint 8 is greatly impeded and thus prevented as far as possible.

In the closed position, the closure system 4 is spring-loaded and elastically pre-stressed. In order to unlock the closure system 4 and to pivot it into the open position, the closure flap 7 has to be pivoted against the pre-stressing force around the first pivot axis S1 or the end of the closure flap 7 facing away from the first pivot joint 6 has to be pulled radially outwards, for example manually with the fingers.

The second pivot joint 8, which is designed as a hinge with joint plates and a pivot pin, is shown in detail in FIG. 2. One end portion of the closure lever 9 has a stop 20 to limit the pivoting movement of the closure lever 9 relative to the closure flap 7. Thus, the closure lever 9 does not pivot completely around the second pivot axis S2 and would hang downwards in accordance with the gravitational force, but remains in the area of the closure flap 7 and can be transferred to the closed position immediately upon closure.

In FIG. 3, as compared to FIG. 2, the closure flap 7 has been pivoted around the first pivot axis S1 out of the closed position in the direction of the open position, and with it the pivotally connected closure lever 9 and the closure-contour part 10 were pivoted as well. The seal 17 is destroyed when the closure flap 7 is opened or pivoted out of the closed position. The closure-contour portion 11 lies closely to the complementary container-contour portion 12. The design of the edge portion 13 of the container vessel 2 as an outwardly bent and circumferential flange transitioning from the walling of the container vessel 2 with bending radii as container-contour portion 12 (optionally circumferential, but channel-like collar) as well as the design of the closure-contour portion 11 with counter radii, allow for a simple movement of the closure system 4, which slides off the container-contour portion 12, when pivoting from an open position into a closed position or vice versa.

FIG. 4 shows the sterile container 1 from FIGS. 2 and 3 in the open position. The container lid 3 can be lifted off again and the sterile container 1 can be opened in this way. The destroyed seal 17 can be removed from the two recesses 14, 15 and a new seal 17 can be inserted in the closed position of the closure system 4, for example after the sterile container 1 has been sterilized again.

FIG. 5 shows a sterile container 101 according to the invention of another/second preferred embodiment. In contrast to the sterile container 1 of the first preferred embodiment, this one has a modified closure system 104 with a modified closure-contour part 110. A closure contour surface 111 in this embodiment is a plane/flat surface without a corresponding outer portion perpendicular to the axis A, as designed in the first embodiment, which only lies in sections against the container contour portion 12 of the edge portion 13 of the container vessel 2 in the closed position.

FIG. 6 and FIG. 7 show the sterile container 101 from FIG. 5 with the inserted seal ring 16 and the inserted seal 17. The functional principle as well as the other components of the sterile container 101 are identical to the sterile container 1 of the first preferred embodiment, which is why reference is made to the above description.

FIG. 8 shows a sterile container 201 according to the invention according to a third preferred embodiment. The sterile container 201 shows a modified closure system 204 with a modified closure flap 207 and a modified closure lever 209 as compared to the first two preferred embodiments. In this embodiment, the closure flap 207 does not have a U-shaped bending, so that the second pivot joint 8 or the second pivot axis S2 on the closure flap 207 in a closed position can be placed further outside with regard to the axis A. The second pivot joint 8 here lies in an extension parallel to the axis A of the first pivot joint 6. The closure flap 207 and the closure lever 209 again have a recess 14 and 15, the longitudinal axis of which points in the closed position towards the axis A, into which a seal which is not shown can be inserted again, similar to the container 1 of the first embodiment. This embodiment does not have a container contact surface 18, so that the closure-contour part 10 can lean against the perpendicular wall of the container vessel 2 at a slight angle (not shown here), i.e. only the lower end of the closure-contour part 10 lies immediately/directly against the wall of the container vessel in order to pre-stress and secure the closure system 4 in the closed position. The closing force, which runs at a slight angle with respect to axis A (see FIG. 1), in combination with the spring force of spring element 21 presses the closure-contour part 10 in the closed position against the wall of the container vessel 2 and thus pre-stresses the closure system 4.

Although the present invention is described above using embodiments, it is understood that various designs and modifications can be made without leaving the scope of the present invention. For example, it is also possible to design another embodiment of a container 1, 101, 201 according to the invention by using more than one closure system 4, 104, 204 to lock the container part 2, 3 and in particular by using different variants of closure systems 4, 104, 204 on a single container 1, 101, 201. An embodiment of a container may also have only one closure system 4, 104, 204 and one pivot joint opposite the closure system 4, 104, 204.

It is also possible that the closure base 5 is designed as a circumferential circle, so that the closure base 5 does not have to be connected to the container lid 3, but can be placed on top as a separate circumferential component.

The invention claimed is:

1. A medical or surgical sterile container comprising a first container part that is a container trough and a second container part that is a container lid, and having at least one closure system comprising a toggle lever arranged on the second container part which is pivotable between a closed position, in which the first container part and the second container part are locked to each other by the at least one closure system, and an open position, in which the first container part and the second container part are unlocked, wherein the first container part has an edge portion that is integrally formed in one piece of material with the first container part on which the at least one closure system is immediately supported in the closed position, for transferring a closing force of the first container part to the second container part, and wherein the at least one closure system is designed such that one arm of the toggle lever is adapted to be pivoted beyond a bottom dead center of an elastic prestress against a side wall of the first container part, thus enabling the closure system to lock itself.

2. The medical or surgical sterile container according to claim 1, wherein the edge portion forms a container-contour portion which defines an undercut, and the at least one closure system has a closure-contour portion which is formed to be complementary to the undercut of the container-contour portion in order to flatly abut on the container-contour portion in the area of the undercut and to engage in a form-fitting manner and to securely lock the first and the second container part together in the closed position.

3. The medical or surgical sterile container according to claim 2, wherein the at least one closure system is attached to the second container part by a closure base, and the closure base has formed therein a first pivot joint with a first pivot axis, to which a closure flap is pivotably attached, and the closure flap comprises a second pivot joint with a second pivot axis, to which a closure lever is pivotably connected, and the closure lever is at an end region supported on the edge portion of the first container part, in order to receive a closing force of the at least one closure system in the closed position and to securely lock the first container part and the second container part together.

4. The medical or surgical sterile container according to claim 3, wherein the first pivot joint and/or the second pivot joint of the at least one closure system is formed by an elastic portion.

5. The medical or surgical sterile container according to claim 3, wherein the first pivot joint and/or the second pivot joint of the at least one closure system is formed by a hinge.

6. The medical or surgical sterile container according to claim 3, wherein the at least one closure system is prepared to accommodate a seal which fixes the closure flap with the closure lever rigidly together when sealing in the closed position in order to secure the at least one closure system against accidental opening in this way.

7. The medical or surgical sterile container according to claim 6, wherein the seal only engages the closure flap and the closure lever without requiring a connection to the first container part or the second container part.

8. The medical or surgical sterile container according to claim 3, wherein a pivoting movement of the closure flap relative to the closure base and/or a pivoting movement of the closure lever relative to the closure flap is limited by a stop to allow simple and efficient locking.

9. The medical or surgical sterile container according to claim 3, wherein a spring element is provided between the closure lever and the closure-contour portion, wherein the spring element in the closed position pre-stresses the at least one closure system against the first container part in order to secure the at least one closure system against unintentional opening, to implement an integrated valve function against an inadmissible internal pressure of the medical or surgical sterile container, and to ensure tolerance compensation.

10. The medical or surgical sterile container according to claim 3, wherein the closure flap and the closure lever in the closed position is mainly parallel to a side wall of the first container part.

11. The medical or surgical sterile container according to claim 3, wherein the closure flap is designed as a bent metal sheet having a U-shaped bending at an end portion facing away from the first pivot joint, so that a free end portion of the closure flap lies closer to the side wall of the first container part in a closed position and is covered radially by a portion of the closure flap, thereby forming a simple handle.

12. The medical or surgical sterile container according to claim 3, wherein the first pivot joint lies, seen in a vertical direction, in an extension of a circumferential outer side of the second container part, so that the first pivot joint allows in the closed position a direct force transmission of the closing force of the first container part and the second container part perpendicular to a plane of an opening of the first container part.

13. The medical or surgical sterile container according to claim 2, wherein the edge portion is a completely circumferential edge.

14. The medical or surgical sterile container according to claim 2, wherein the edge portion is deep-drawn.

15. The medical or surgical sterile container according to claim 2, wherein the closure-contour portion is directly resting on a sidewall of the first container part.

16. The medical or surgical sterile container according to claim 1, wherein the edge portion of the first container part is made of a metallic material.

17. The medical or surgical sterile container according to claim 1, wherein the at least one closure system is adapted to accommodate a seal which secures the at least one closure system against accidental opening when sealing in the closed position.

18. The medical or surgical sterile container according to claim 1, wherein the closure system comprises a spring-loaded closure-contour portion.

19. The medical or surgical sterile container according to claim 1, wherein the closure system comprises a first arm and a second arm, the first arm and the second arm being in plate form and coupled to each other in a hinge manner, of which the first arm is hinged to an edge region of the second container part and the second arm has at its free end as a closure-contour-portion a support foot that engages in the edge portion on the first container part that is in the form of an undercut, thereby, when the first arm is folded down towards the first container part while the support foot is already supported on the undercut, the support foot is pressed against the undercut as a toggle-lever mechanism and thus pulls the second container part against the first container part.

20. The medical or surgical sterile container according to claim 1, wherein a closing force runs obliquely from radially further inwards on the first container part, which is arranged further down relative to the second container part, towards radially further outwards on the second container part that results in self-locking or pre-stressing of the closure system in the closed position.

* * * * *